United States Patent
Babu et al.

(10) Patent No.: US 9,315,471 B2
(45) Date of Patent: Apr. 19, 2016

(54) PROCESS OF MAKING HYDROXYLATED CYCLOPENTAPYRIMIDINE COMPOUNDS AND SALTS THEREOF

(71) Applicant: Genentech, Inc., South San Francisco, CA (US)

(72) Inventors: Srinivasan Babu, South San Francisco, CA (US); Francis Gosselin, South San Francisco, CA (US); Yingqing Ran, South San Francisco, CA (US); Travis Remarchuk, South San Francisco, CA (US); Scott J. Savage, South San Francisco, CA (US); Jeffrey Stults, South San Francisco, CA (US); Herbert Yajima, South San Francisco, CA (US)

(73) Assignee: GENETECH, INC., South San Francisco, CA (US)

(*) Notice: Subject to any disclaimer, the term of this patent is extended or adjusted under 35 U.S.C. 154(b) by 0 days.

(21) Appl. No.: 14/401,089

(22) PCT Filed: May 17, 2013

(86) PCT No.: PCT/US2013/041695
§ 371 (c)(1),
(2) Date: Nov. 13, 2014

(87) PCT Pub. No.: WO2013/173784
PCT Pub. Date: Nov. 21, 2013

(65) Prior Publication Data
US 2015/0099880 A1 Apr. 9, 2015

Related U.S. Application Data

(60) Provisional application No. 61/648,535, filed on May 17, 2012.

(51) Int. Cl.
C07D 239/70 (2006.01)
C07D 403/04 (2006.01)
C12P 17/16 (2006.01)

(52) U.S. Cl.
CPC ............ *C07D 239/70* (2013.01); *C07D 403/04* (2013.01); *C12P 17/165* (2013.01)

(58) Field of Classification Search
None
See application file for complete search history.

(56) References Cited

U.S. PATENT DOCUMENTS

| 7,169,928 | B2 | 1/2007 | Schwartz et al. |
| 8,063,050 | B2 | 11/2011 | Mitchell et al. |
| 2011/0281844 | A1 | 11/2011 | Schwartz et al. |
| 2012/0149684 | A1 | 6/2012 | Beight et al. |
| 2014/0121193 | A1 | 5/2014 | Katz et al. |
| 2015/0099881 | A1 | 4/2015 | Lane et al. |
| 2015/0148559 | A1 | 5/2015 | Remarchuk et al. |
| 2015/0152067 | A1 | 6/2015 | Askin et al. |

FOREIGN PATENT DOCUMENTS

| EP | 0918090 A2 | 5/1999 |
| WO | WO 95/15684 | 6/1995 |
| WO | WO 98/44797 | 10/1998 |
| WO | WO 98/56234 | 12/1998 |
| WO | WO 00/52134 | 9/2000 |
| WO | WO 01/22963 | 4/2001 |
| WO | WO 02/086126 A2 | 10/2002 |
| WO | WO 2004/108673 | 12/2004 |
| WO | WO 2008/006040 A1 | 1/2008 |
| WO | WO 2009/047255 | 4/2009 |
| WO | WO 2009/089453 A1 | 7/2009 |
| WO | WO 2010/120935 | 10/2010 |
| WO | WO 2012/009649 | 1/2012 |
| WO | WO 2012/040258 | 3/2012 |
| WO | WO 2012/177925 | 12/2012 |
| WO | WO 2014/127350 | 8/2014 |
| WO | WO 2014/150395 | 9/2014 |

OTHER PUBLICATIONS

Bastin, et al., "Salt Selection and Optimisation Procedures for Pharmaceutical New Chemical Entities", Organic Process Research & Development 4, 427-435 (2000).
Haleblian, et al., "Characterization of Habits and Crystalline Modification of Solids and Their Pharmaceutical Applications", Journal of Pharmaceutical Sciences, vol. 64 (8), 1269-1288 (1975).
Vippagunta, et al., "Crystalline solids", Advanced Drug Delivery Reviews 48, 3-26 (2001).
Dunetz et al., "General and Scalable Amide Bond Formation with Epimerization-Prone Substrates Using T3P and Pyridine", *Organic Letters*, vol. 13 (19), 5048-5051 (2011).
Patent Cooperation Treaty, International Searching Authority, Search Report and Written Opinion for PCT/US2013/041695, 15 pages, Nov. 5, 2013.

*Primary Examiner* — Jeffrey H Murray
(74) *Attorney, Agent, or Firm* — Viksnins Harris & Padys PLLP (57) ABSTRACT

The invention provides new processes for making and purifying salts of hydroxylated cyclopentapyrimidine compounds, which are useful as AKT inhibitors used in the treatment of diseases such as cancer, including the monohydrochloride salt of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one.

16 Claims, 3 Drawing Sheets

PROCESS OF MAKING HYDROXYLATED CYCLOPENTAPYRIMIDINE COMPOUNDS AND SALTS THEREOF

PRIORITY OF INVENTION

This application claims priority to U.S. Provisional Application No. 61/648,535 that was filed on 17 May 2012. The entire content of this provisional application is hereby incorporated herein by reference.

FIELD OF THE INVENTION

Disclosed herein are processes for making and purifying hydroxylated cyclopentapyrimidine compounds for the synthesis of inhibitors of AKT kinase activity.

BACKGROUND OF THE INVENTION

The Protein Kinase B/Akt enzymes are a group of serine/threonine kinases that are overexpressed in certain human tumors. International Patent Application Publication Number WO 2008/006040 and U.S. Pat. No. 8,063,050 discuss a number of inhibitors of AKT, including the compound (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one. While processes described in WO 2008/006040 and U.S. Pat. No. 8,063,050 are useful in providing hydroxylated cyclopenta[d]pyrimidine compounds as AKT protein kinase inhibitors, alternative or improved processes are needed, including for large scale manufacturing of these compounds and their intermediates. Additionally, the dihydrochloride salt of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one is difficult to prepare in a form other than the amorphous form, and is hygroscopic making it difficult to process into drug forms. Therefore, what is also needed are additional salts and forms of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one that have improved pharmaceutical properties such as stable, crystalline forms.

BRIEF SUMMARY OF THE INVENTION

Disclosed are processes for preparing, separating and purifying compounds detailed herein. Compounds provided herein include AKT protein kinase inhibitors, salts thereof, and intermediates useful in the preparation of such compounds.

One aspect includes a process comprising reducing a compound of formula II, or a salt thereof:

wherein $R^1$ is defined herein to form a compound of formula III:

or a salt thereof.

Another aspect includes a process that includes deptrotecting a compound of formula III or a salt thereof, wherein $R^1$ is an amino protecting group, to form a compound of formula IIIa or salt thereof.

Another aspect includes a process that includes reacting a compound of formula IIIa or salt thereof with a compound of formula IV or salt thereof to form a compound of formula I or salt thereof,

I wherein R² in formulae IV and I is independently hydrogen or an amino protecting group.

Another aspect includes a process for preparing a salt of a compound of formula Ia:

Ia the process comprising contacting a compound of formula I (wherein R² is hydrogen or an amino protecting group) with acid to form the salt of the compound of formula Ia, wherein R² is hydrogen.

Another aspect includes a process for preparing a monohydrochloride salt of a compound of formula Ia:

Ia the process comprising contacting a compound of formula I, wherein R² is an amino protecting group, with acid to form the dihydrochloride salt, wherein R² is hydrogen, and contacting the dihydrochloride salt with base to form the monohydrochloride salt.

Another aspect includes the monohydrochloride salt of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one.

Another aspect includes (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one benzene sulfonic acid salt. In one example, the benzene sulfonic acid salt is crystalline.

Another aspect includes (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one p-toluene sulfonic acid salt. In one example, the p-toluene sulfonic acid salt is crystalline.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. In the event that one or more of the incorporated literature and similar materials differs from or contradicts this application, including but not limited to defined terms, term usage, described techniques, or the like, this application controls.

The term "alkyl" as used herein refers to a saturated linear or branched-chain monovalent hydrocarbon radical of one to twelve carbon atoms, and in another embodiment one to six carbon atoms, wherein the alkyl radical may be optionally substituted independently with one or more substituents described herein. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, and the like.

The term "alkylene" as used herein refers to a linear or branched saturated divalent hydrocarbon radical of one to twelve carbon atoms, and in another embodiment one to six carbon atoms, wherein the alkylene radical may be optionally substituted independently with one or more substituents described herein. Examples include, but are not limited to, methylene, ethylene, propylene, 2-methylpropylene, pentylene, and the like.

The term "alkenyl" as used herein refers to a linear or branched-chain monovalent hydrocarbon radical of two to twelve carbon atoms, and in another embodiment two to six carbon atoms, with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2CH$=$CH_2$), 1-propenyl, 1-buten-1-yl, 1-buten-2-yl, and the like.

The term "alkynyl" as used herein refers to a linear or branched monovalent hydrocarbon radical of two to twelve carbon atoms, and in another embodiment two to six carbon atoms, with at least one site of unsaturation, i.e., a carbon-carbon, sp triple bond, wherein the alkynyl radical may be optionally substituted independently with one or more substituents described herein. Examples include, but are not limited to, ethynyl (—C≡CH) and propynyl (propargyl, —$CH_2$C≡CH).

The term "alkoxy" refers to a linear or branched monovalent radical represented by the formula —OR in which R is alkyl, alkenyl, alkynyl or cycloalkyl, which can be further optionally substituted as defined herein. Alkoxy groups include methoxy, ethoxy, propoxy, isopropoxy, mono-, di- and tri-fluoromethoxy and cyclopropoxy.

"Amino" means primary (i.e., —$NH_2$), secondary (i.e., —NRH), tertiary (i.e., —NRR) and quaternary (i.e., —$N^+RRRX^-$) amines, that are optionally substituted, in which R is independently alkyl, alkoxy, a cycloalkyl, a heterocyclyl, cycloalkyl, -substituted alkyl or heterocyclyl-substituted alkyl wherein the alkyl, alkoxy, cycloalkyl and heterocyclyl are as defined herein Particular secondary and tertiary amines are alkylamine, dialkylamine, arylamine, diarylamine, aralkylamine and diaralkylamine wherein the alkyls and aryls are as herein defined and independently optionally substituted. Particular secondary and tertiary amines are methylamine, ethylamine, propylamine, isopropylamine, phenylamine, benzylamine dimethylamine, diethylamine, dipropylamine and diisopropylamine.

The terms "cycloalkyl," "carbocycle," "carbocyclyl" and "carbocyclic ring" as used herein are used interchangeably and refer to saturated or partially unsaturated cyclic hydrocarbon radical having from three to twelve carbon atoms, and in another embodiment from three to 7 carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl ring fused to a saturated, partially unsaturated or aromatic cycloalkyl or heterocyclic ring. Examples of cycloalkyl groups include, but are not limited to, cyclopropyl, cyclobutyl, cyclopentyl, cyclohexyl, cycloheptyl, cyclohexenyl, cyclohexadienyl, cycloheptenyl, and the like. Bicyclic carbocycles include those having 7 to 12 ring atoms arranged, for example, as a bicyclo [4,5], [5,5], [5,6] or [6,6] system, or as bridged systems such as bicyclo[2.2.1] heptane, bicyclo[2.2.2]octane, and bicyclo[3.2.2]nonane. The cycloalkyl may be optionally substituted independently with one or more substituents described herein.

The term "aryl" as used herein means a monovalent aromatic hydrocarbon radical of 6-20 carbon atoms derived by the removal of one hydrogen atom from a single carbon atom of a parent aromatic ring system. Aryl includes bicyclic radicals comprising an aromatic ring fused to a saturated, partially unsaturated ring, or aromatic carbocyclic or heterocyclic ring. Exemplary aryl groups include, but are not limited to, radicals derived from benzene, naphthalene, anthracene, biphenyl, indene, indane, 1,2-dihydronapthalene, 1,2,3,4-tetrahydronapthalene, and the like. Aryl groups may be optionally substituted independently with one or more substituents described herein.

The terms "heterocycle", "hetercyclyl" and "heterocyclic ring" as used herein are used interchangeably and refer to a saturated or partially unsaturated carbocyclic radical of 3 to 12 ring atoms in which at least one ring atom is a heteroatom independently selected from nitrogen, oxygen and sulfur, the remaining ring atoms being C, where one or more ring atoms may be optionally substituted independently with one or more substituents described below. In one embodiment, heterocyclyl includes 3 to 7 membered ring atoms in which at least one ring atom is a heteroatom independently selected from nitrogen, oxygen and sulfur, the remaining ring atoms being C, where one or more ring atoms may be optionally substituted independently with one or more substituents described below. The radical may be a carbon radical or heteroatom radical. The term "heterocycle" includes heterocycloalkoxy. "Heterocyclyl" also includes radicals where heterocycle radicals are fused with a saturated, partially unsaturated, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. The heterocycle may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). Examples of heterocyclic groups wherein 2 ring carbon atoms are substituted with oxo (=O) moieties are isoindoline-1,3-dionyl and 1,1-dioxo-thiomorpholinyl. The heterocycle groups herein are optionally substituted independently with one or more substituents described herein.

The term "heteroaryl" as used herein refers to a monovalent aromatic radical of a 5-, 6-, or 7-membered ring and includes fused ring systems (at least one of which is aromatic) of 5-10 atoms containing at least one heteroatom independently selected from nitrogen, oxygen, and sulfur. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups may be optionally substituted independently with one or more substituents described herein.

"Amino-protecting group" as used herein refers to groups commonly employed to keep amino groups from reacting during reactions carried out on other functional groups. Examples of such protecting groups include carbamates, amides, alkyl and aryl groups, imines, as well as many N-heteroatom derivatives which can be removed to regenerate the desired amine group. Particular amino protecting groups are Ac (acetyl), trifluoroacetyl, phthalimide, Bn (benzyl), Tr (triphenylmethyl or trityl), benzylidenyl, p-toluenesulfonyl, Pmb (p-methoxybenzyl), Boc (tert-butyloxycarbonyl), Fmoc (9-fluorenylmethyloxycarbonyl) and Cbz (carbobenzyloxy). Further examples of these groups are found in: Wuts, P. G. M. and Greene, T. W. (2006) Frontmatter, in Greene's Protective Groups in Organic Synthesis, Fourth Edition, John Wiley & Sons, Inc., Hoboken, N.J., USA. The term "protected amino" refers to an amino group substituted with one of the above amino-protecting groups.

The term "substituted" as used herein means any of the above groups (e.g., alkyl, alkylene, alkenyl, alkynyl, cycloalkyl, aryl, heterocyclyl and heteroaryl) wherein at least one hydrogen atom is replaced with a substituent. In the case of an oxo substituent ("=O") two hydrogen atoms are replaced. "Substituents" within the context of this invention include, but are not limited to, halogen, hydroxy, oxo, cyano, nitro, amino, alkylamino, dialkylamino, alkyl, alkenyl, alkynyl, cycloalkyl, alkoxy, substituted alkyl, thioalkyl, haloalkyl (including perhaloalkyl), hydroxyalkyl, aminoalkyl, substituted alkenyl, substituted alkynyl, substituted cycloalkyl, aryl, substituted aryl, heteroaryl, substituted heteroaryl, heterocycle, substituted heterocycle, —NR$^e$R$^f$, —NR$^e$C(=O) R$^f$, —NR$^e$C(=O)NR$^e$R$^f$, —NR$^e$C(=O)OR$^f$—NR$^e$SO$_2$R$^f$, —OR$^e$, —C(=O)R$^e$—C(=O)OR$^e$, —C(=O)NR$^e$R$^f$, —OC(=O)R$^e$R$^f$, —SR$^e$, —SOR$^B$, —S(=O)$_2$R$^e$, —OS(=O)$_2$R$^e$, —S(=O)$_2$OR$^e$, wherein R$^e$ and R$^f$ are the same or different and independently hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocycle, substituted heterocycle.

The term "halo" or "halogen" as used herein means fluoro, chloro, bromo or iodo.

The term "a" as used herein means one or more.

Reference to "about" a value or parameter herein includes (and describes) embodiments that are directed to that value or parameter per se. For example, description referring to "about X" includes description of "X".

"Pharmaceutically acceptable salts" include both acid and base addition salts. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound.

"Pharmaceutically acceptable acid addition salt" refers to those salts which retain the biological effectiveness and properties of the free bases and which are not biologically or otherwise undesirable, formed with inorganic acids such as nicotinic acid, hippuric acid, hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid, nicotinic acid, hippuric acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the nicotinamide, picolinamide, benzamide, ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, tromethamine, dicyclohexylamine, choline, and caffeine.

Compounds of the present invention, unless otherwise indicated, include compounds that differ only in the presence of one or more isotopically enriched atoms. For example, compounds of the present invention, wherein one or more hydrogen atoms are replaced by deuterium or tritium, or one or more carbon atoms are replaced by a $^{13}C$ or $^{14}C$ carbon atom, or one or more nitrogen atoms are replaced by a $^{15}N$ nitrogen atom, or one or more sulfur atoms are replaced by a $^{33}S$, $^{34}S$ or $^{36}S$ sulfur atom, or one or more oxygen atoms are replaced by a $^{17}O$ or $^{18}O$ oxygen atom are within the scope of this invention.

One aspect includes a process that includes stereoselectively reducing a compound of formula II or a salt thereof:

II wherein:
R$^1$ is hydrogen or an amino protecting group;
to form a compound of formula III:

III or a salt thereof.

In certain embodiments, R$^1$ is hydrogen.
In certain embodiments, R$^1$ is an amino protecting group. In certain embodiments, R$^1$ is acetyl (Ac), trifluoroacetyl, phthalimide, benzyl (Bn), trityl (Tr), benzylidenyl, p-toluenesulfonyl, para-methoxy benzyl (Pmb), t-butoxycarbonyl (Boc), Fluorenylmethyloxycarbonyl (Fmoc) or Carboxybenzyl (Cbz). In certain embodiments, R$^1$ is Boc group.

In certain embodiments, the process of stereoselectively reducing a compound of formula II or a salt thereof includes contacting the compound of formula II, or a salt thereof, with a reducing agent.

In certain embodiments, the reducing agent comprises an enzyme.

In certain embodiments, the reducing agent comprises an enzyme that promotes or directs stereo selectivity of the reduction of the compound of formula II or a salt thereof.

In certain embodiments, the reducing agent comprises an enzyme and hydride source. In one aspect, the enzymatic reducing agent comprises a ketoreductase enzyme, which may be a natural or genetically engineered enzyme. Ketoreductase enzymes participate in the stereoselective reduction of a carbonyl group, such as the stereoselective reduction of a ketone or an alcohol. Such enzymes include CRED (carbonylreductase) and KRED (ketoreductase) enzymes. A carbonylreductase or ketoreductase enzyme may be used with any suitable cofactor. In one aspect, the co-factor is NADH or NADPH. In one aspect, the ketoreductase enzyme is a NADPH-dependent ketoreductase enzyme that is used in conjunction with NADPH as a co-factor. However, it is understood that a NADPH-dependent ketoreductase enzyme may also be used in conjunction with cofactors other than NADPH, such as NADH. In another aspect, the ketoreductase enzyme is a NADH-dependent ketoreductase enzyme. However, it is understood that a NADH-dependent ketoreductase enzyme may also be used in conjunction with cofactors other than NADH, such as NADPH. In a particular variation, the reducing agent comprises a cofactor such as NADH or NADPH used in conjunction with an carbonylreductase or ketoreductase enzyme such as KRED-101, KRED-112, KRED-113, KRED-114, KRED-115, KRED-121, KRED-123, KRED-124, KRED-130, KRED-132, KRED-133, KRED-135, KRED-142, KRED-145 and KRED-153 (all commercially available from Codexis Inc, Redwood City, Calif., USA). In a particular variation, the reducing agent is NADPH used in conjunction with a carbonylreductase or ketoreductase enzyme such as KRED-101, KRED-112, KRED-113 and KRED-114. In another variation, the reducing agent comprises a cofactor such as NADH or NADPH used in conjunction with a carbonylreductase or ketoreductase enzyme such as KRED-107, KRED-108, KRED-109, KRED-110, KRED-116, KRED-121 and KRED-125 (all commercially available from Codexis Inc, Redwood City, Calif., USA). Other suitable carbonylreductase or ketoreductase enzymes may be used, such as Codexis-134, Codexis-150, Codexis-168, Codexis-112, Codexis-102, Codexis-151, Codexis-123, Codexis-103, Codexis-119, Codexis-128, Codexis-136, Codexis-174, Codexis-105, Codexis-129, Codexis-137, Codexis-161, Codexis-176, Codexis-154, Codexis-106, Codexis-131, Codexis-155, Codexis-148, Codexis-165, Codexis-129, Codexis-108, Codexis-116, Codexis-125, Codexis-149, Codexis-111, DAICEL-E073, DAICEL-E087, BCC 111, C-LEcta-ADH-44s, DAICEL-E005, DAICEL-E077, C-LEcta-ADH-24s, BCC 103, C-LEcta-ADH-14s, C-LEcta-ADH-16s, DAICEL-E007, DAICEL-E008, DAICEL-E080, DAICEL-E082, DAICEL-E052, BCC 101, C-LEcta-ADH-48s, BCC 109, EVO-1.1.211, DAICEL-E072 and C-LEcta-ADH-50s. Other suitable enzymes include alcohol dehydrogenase enzymes including ADH-1, ADH-2, ADH-3, ADH-A, ADH-B, ADH-III (available from DSM). Other suitable enzymes may be identified by methods known in the art. Suitable commerically available enzymes may be used, such as those that are commercially available from sources such as Codexis Inc, Redwood City, Calif., USA, and Almac Group Ltd., United Kingdom.

Sources of hydrogen include hydrogen gas, and other sources used in transfer hydrogenation reactions, including water (optionally with formate or acetate salts such as sodium formate), diimide, hydrazine (or hydrazine hydrate), alcohols, such as methanol, ethanol and isopropanol, cycloalkenes, such as cyclohexene, cyclohexadiene, dihydronaphthalene and dihydroanthracene, organic acids (optionally with an amine such as trimethyl- or triethyl-amine), such as formic acid, acetic acid or phosphoric acid, silanes such as HSiR$_3$ (where R is independently an alkyl group, such as HSiMe$_3$ and HSiEt$_3$), NADH, NADPH, FADH$_2$, ammonium salts, such as ammonium formate and ammonium chloride, and Hanztch esters such as those of the formula:

wherein $R^{11}$, $R^{12}$, $R^{13}$ and $R^{14}$ are independently alkyl (In certain examples: $R^{11}$ and $R^{12}$ are methyl and $R^{13}$ and $R^{14}$ are ethyl; $R^{11}$ and $R^{12}$ are methyl and $R^{13}$ and $R^{14}$ are butyl; $R^{11}$ is methyl, $R^{12}$ is isopropyl and $R^{13}$ and $R^{14}$ are methyl; $R^{11}$ and $R^{12}$ are methyl, $R^{13}$ is methyl and $R^{14}$ is t-butyl; $R^{11}$ and $R^{12}$ are methyl and $R^{13}$ and $R^{14}$ are methyl; $R^{11}$ and $R^{12}$ are methyl and $R^{13}$ and $R^{14}$ are isobutyl; $R^{11}$ and $R^{12}$ are methyl and $R^{13}$ and $R^{14}$ are allyl).

Another aspect includes a process that includes deptrotecting a compound of formula III or a salt thereof wherein $R^1$ is an amino protecting group, to form a compound of formula IIIa or a salt thereof.

Another aspect includes a process that includes reacting a compound of formula IIIa or salt thereof with a compound of formula IV or salt thereof to form a compound of formula I or salt thereof:

wherein $R^2$ in formulae IV and I is independently hydrogen or an amino protecting group.

In certain embodiments, $R^2$ is hydrogen.

In certain embodiments, $R^2$ is an amino protecting group. In certain embodiments, $R^2$ is Ac, trifluoroacetyl, phthalimide, Bn, Tr, benzylidenyl, p-toluenesulfonyl, Pmb, Boc, Fmoc or Cbz. In certain embodiments, $R^2$ is Boc group.

Methods of making a compound of the formula IV or a salt thereof are described in U.S. Pat. No. 8,063,050, issued Nov. 22, 2011 to Mitchell (e.g., in Scheme A and Example 14).

The process of making a compound of formula I, or a salt thereof, in one aspect includes conditions for amide bond formation comprising a coupling agent. In certain embodiments, the process further comprises a base, such as those described herein, for example an organic amine base, such as methylmorpholine. For example, the coupling reaction may be carried out using a peptide coupling reagent selected from carbonyl-diimidazole, carbonyl-diimidazole with N-methylimidazole, 2-chloro-4,6-dimethoxy-1,3,5-triazone, 1-ethyl-3-(3-dimethylaminopropyl)carbodiimide, 1-ethyl-3-(3-dimethylaminopropyl)carbodiimide with N-methylimidazole, 1-ethyl-3-(3-dimethylaminopropyl)carbodiimide with hydroxybenzotriazole isobutylchloroformate, propanephosphonic anhydride, and propanephosphonic anhydride with 4-methylmorpholine.

In one embodiment, the coupling agent comprises propanephosphonic anhydride.

In one embodiment, the coupling agent comprises propanephosphonic anhydride and 4-methylmorpholine.

Another aspect includes a process for preparing a salt of a compound of formula Ia the process comprising contacting a compound of formula I, wherein $R^2$ is an amino protecting group, with acid to form the salt of the compound of formula Ia, wherein $R^2$ is hydrogen.

Another aspect includes salts of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one, wherein the salt is selected from mono hydrochloride, di hydrochloride, mono tosylate, mono mesylate, mono besylate, bis hexafluorophosphate, mono oxalate, mono sulphuric, bis sulphuric, mono phosporic, bis phosphoric, mono glutamic, mono malonic, mono L-tartaric, mono fumaric, mono citric, mono L-malic, mono D-gluconic, mono-lactic, mono succinic and mono adipic salt.

Another aspect includes (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one benzene sulfonic acid salt. In one example, the benzene sulfonic acid salt is crystalline.

Another aspect includes (S)-2-(4-chlorophenyl)-1-(4-((5R,7R)-7-hydroxy-5-methyl-6,7-dihydro-5H-cyclopenta

[d]pyrimidin-4-yl)piperazin-1-yl)-3-(isopropylamino)propan-1-one p-toluene sulfonic acid salt. In one example, the p-toluene sulfonic acid salt is crystalline.

Another aspect includes a process for preparing a crystalline form of a salt of a compound of formula Ia, the process comprising contacting a compound of formula Ia, with acid to form a salt of compound of formula Ia. In one example, the salt when isolated is amorphous. In certain embodiments, the process further comprises contacting the salt with solvent to form the crystalline form of the salt of the compound of formula Ia. In one example, the salt is a mono-benzene sulfonic acid salt. In another example, the salt is a mono-p-toluene sulfonic acid salt. In another example, the solvent used to crystallize the salt is acetonitrile or nitromethane.

Another aspect includes a process for preparing a mono-salt of a compound of formula Ia, the process comprising contacting a compound of formula I, wherein $R^2$ is an amino protecting group with acid to form a bis-salt of compound of formula Ia; and contacting the bis-salt with base to form the mono-salt of the compound of formula Ia, wherein $R^2$ is hydrogen. In one example, hydrochloric acid is used as the acid, the bis-salt formed is dihydrochloride salt, and the final product is the monohydrochloride salt of a compound of formula Ia.

Another aspect includes a process for preparing a monohydrochloride salt of a compound of formula Ia, the process comprising contacting a compound of formula I, wherein $R^2$ is an amino protecting group with hydrochloric acid to form the dihydrochloride salt; and contacting the dihydrochloride salt with base to form the monohydrochloride salt of the compound of formula Ia, wherein $R^2$ is hydrogen.

Another aspect includes the monohydrochloride salt of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one.

Bases for use in the process for converting the dihydrochloride salt of formula Ia to the monohydrochloride salt of formula Ia include organic bases, inorganic bases and resinous bases. Organic bases include amine bases such as ammonia, alkyl amines, for example methyl amine, dimethyl amine, diethyl amine, trimethyl amine, triethyl amine, butyl amine, tetra-methylethyldiamine, isopropyl amine and diisopropyl amine, aniline, indole, pyridine, pyrimidine, pyrrolidine, N-methylpyrrolidone, pyrrole, pyrazole, imidazole, morpholine, N-methylmorpholine, piperidine, piperazine, N,N-dimethylpiperizine, and the like. Inorganic bases include bicarbonate, carbonate and hydroxide bases, for example, ammonium hydroxide, ammonium carbonate, barium hydroxide, barium carbonate, calcium carbonate, calcium hydroxid, cesium carbonate, cesium hydroxide, lithium amide, lithium carbonate, lithium hydroxide, magnesium hydroxide, magnesium carbonate, potassium hydroxide, potassium bicarbonate, potassium carbonate, sodium bicarbonate, sodium carbonate, sodium hydroxide, sodium amide and soda lime.

In certain embodiments, the base in the process for converting the dihydrochloride salt of formula Ia to the monohydrochloride salt of formula Ia comprises a resinous base.

In certain embodiments, the process for converting the dihydrochloride salt to the monohydrochloride salt comprises contacting the compound of formula Ia, or a salt thereof, with a polymeric resin to form the monohydrochloride salt of formula Ia. In certain embodiments, the polymeric resin comprises functionalized styrene divinylbenzene copolymers, examples of which are commercially available (Amberlyst series, e.g., Amberlyst A-21 and Amberlite FPA51, available from Dow Chemical, Midland, Mich.).

Scheme 1 shows a general method for preparing the compounds of the present invention. For a more detailed description of the individual reaction steps, see the Examples section below. Although specific starting materials and reagents are depicted in the Scheme and discussed below, other starting materials and reagents can be easily substituted to provide a variety of derivatives and/or reaction conditions.

Scheme 1

As shown in Scheme 1, a compound of formula II can be stereoselectively reduced to the alcohol of formula III with a ketoreductase. The compound of formula III can be deprotected with acid (where $R^1$ is an amino protecting group) to form a de-protected form of the alcohol of formula IIIc (where $R^1$ is hydrogen), for example hydrochloric acid. Deprotected compounds of formula III or IIIa can be coupled with a compound of formula IV using a coupling agent, for example propanephosphonic anhydride, to form a compound of formula I. Compounds of formula I can be deprotected or functionalized to form the deprotected form or salt form compound Ia, wherein $R^2$ is hydrogen, with acid.

Also detailed herein is a product produced by any process, scheme or example provided herein. For example, in one aspect is provided a product produced by the process of: contacting the compound of formula II, or a salt thereof, with a reducing agent to form a compound of formula III, or a salt thereof; contacting the compound of formula III, or a salt thereof, with a compound of formula IV, or a salt thereof to form a compound of formula I or salt thereof; contacting the compound of formula I, or a salt thereof, with acid to form a salt form of compound of formula Ia; and contacting a bis salt of the compound of formula Ia with base to form a mono salt form.

EXAMPLES

The invention can be further understood by reference to the following examples, which are provided by way of illustration and are not meant to be limiting.

Abbreviations used herein are as follows:
CPME: Cyclopentyl methyl ether
GDH: glutamate dehydrogenase
IPA: isopropylalcohol
NADP: Nicotinamide adenine dinucleotide phosphate
TLC: thin layer chromatography
HPLC: high pressure liquid chromatography Example 1 tert-butyl 4-((5R,7R)-7-hydroxy-5-methyl-6,7-dihydro-5H-cyclopenta[d]pyrimidin-4-yl)piperazine-1-carboxylate A 3000 L glass-lined reactor was evacuated and filled with nitrogen to normal pressure 3 times. Water (660.0 kg) was added into the reactor while maintaining the temperature in the range of 20-30° C. The stirrer was started, followed by the addition of potassium dihydrogen phosphate (9.2 kg), dipotassium phosphate (23.7 kg) and glucose (78.5 kg). The mixture was stirred until solid dissolved completely. Then 30.1 kg of this buffer mixture was discharged into a 50 L drum for future use. To the reactor was added (R)-tert-butyl 4-(5-methyl-7-oxo-6,7-dihydro-5H-cyclopenta[d]pyrimidin-4-yl) piperazine-1-carboxylate (66.0 kg) and PEG400 (732.6 kg) and the mixture was heated to about 30-35° C. Maintaining the temperature at 30-35° C., a mixture of buffer solution (20.0 kg), KRED-101 (2.4 kg), GDH (3.4 kg) and NADP (2.2 kg) was added into the mixture. The mixture was then maintained at 32-37° C. for reaction while controlling the pH at 6.8-7.1. After about 6 h, the mixture was monitored by TLC and HPLC until ketone starting substrate was ≤1.0%. During the reaction, potassium hydroxide solution (total 46.2 kg) and extra enzyme buffer solution prepared with purified water (5.0 kg), KRED-101 (0.24 kg), GDH (0.34 kg) and NADP (0.22 kg) were added.

To a glass-lined reactor, isopropyl acetate (1148.6 kg) was added. The reaction mixture from the previous paragraph was added to the reactor in three portions. Each time, it was stirred for 15-20 min and held for at least 0.5 h before separation at 20-30° C. This extraction process was repeated three times. The organic phases were combined. At 20-30° C., the combined organic phases were washed with purified water (329.3 kg). It was stirred for 25-30 min and held for at least 30 min before separation. The organic phase was left in the reactor and the washing process was repeated. The organic phase was decolorized with active carbon (6.6 kg) and stirred for 1-1.5 h. The mixture was filtered via a Nutsche filter. The cake was washed with isopropyl acetate (57.5 kg). The filtrates were combined. The filtrate was then transferred into a thin film evaporator and concentrated at ≤55° C. under reduced pressure until 500-600 L remained. The concentrated mixture was filtered and transferred into a glass-lined reactor, then concentrated at ≤55° C. under reduced pressure until 50-60 L remained. The mixture was then heated to 50-55° C. and stirred at this temperature for 0.5-1.5 h under nitrogen. n-Heptane (277.2 kg) was added into the mixture at the rate of 20-30 kg/h while maintaining the temperature at 50-55° C. The mixture was then cooled to 20-30° C. at the rate of 5-10° C./h. The mixture was stirred at 20-30° C. for 1 h, then heated to 50-55° C. and stirrer for 1-2 h, and then cooled to 15-20° C. at a rate of 5-10° C./h for crystallization. It was sampled to be analyzed by HPLC every 1-2 h until wt % of the mother liquid was ≤3% or the change of the wt % between consecutive samples was ≤0.5%. The mixture was then filtered with a centrifuge. The filter cake was washed with n-heptane (45.0 kg). The filtrate was transferred into a glass-lined reactor and concentrated at ≤45° C. under reduced pressure (≤−0.06 MPa) until no more distillate was observed (approximately 20 L remained). Isopropyl acetate (20.0 kg) was added, the mixture was heated to 45-55° C. and stirred for 0.5-1 h. The mixture was dried at 40-50° C. to give tert-butyl 4-((5R,7R)-7-hydroxy-5-methyl-6,7-dihydro-5H-cyclopenta[d]pyrimidin-4-yl)piperazine-1-carboxylate as grey solid (50.65 kg, 76.3% yield), HPLC rt=18.93 min, 99.9% pure, 100% de, 100% ee. The HPLC conditions are given in Table 1 below.

TABLE 1

| Column | ACE-3-C18 column, 4.6 × 150 mm, 3 μm |
|---|---|
| Column temperature | 30° C. |
| Mobile phase | Mobile Phase A: 20 mM ammonium formate at pH 3.7 |
| | Mobile Phase B: methanol (MeOH) 0.8 mL/min |
| Flow Rate | |
| Run Time | 27 min |
| Gradient | Time (min) | % B |

| Time (min) | % B |
|---|---|
| 0 | 5 |
| 5 | 30 |
| 20 | 80 |
| 26 | 100 |
| 29 | 100 |
| 29.1 | 5 |
| 34 | 5 |

Example 2 tert-butyl ((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)(isopropyl)carbamate To a three-neck 250 mL round bottom flask, equipped with a mechanical stirrer, a nitrogen inlet, and a thermocouple was charged tert-butyl 4-((5R,7R)-7-hydroxy-5-methyl-6,7-dihydro-5H-cyclopenta[d]pyrimidin-4-yl)piperazine-1-carboxylate (9.8 g, 29.3 mmol), 2-propanol (41.6 mL) and 2.75 M HCl in 2-propanol (32 mL, 88 mmol). The mixture was heated to 55-65° C. until reaction completion. Distilled 2-propanol (~13%) to remove excess HCl. The reaction mixture was cooled to 5° C. and added 4-methylmorpholine (21 mL, 191 mmol) at a rate maintaining the temperature below 25° C. The mixture was stirred at room temperature for 30 min. (S)-3-((tert-butoxycarbonyl)(isopropyl)amino)-2-(4-chlorophenyl)propanoic acid (10.5 g, 30.8 mmol) and 2-propanol (24.5 mL) were added and the reaction mixture was cooled 0-5° C. Additional 2-propanol was added as required for rinse and to dilute reaction mixture to 10 vol total. Propanephosphonic anhydride (T3P) (50 wt % in EtOAc) (19.2 mL, 32.2 mmol) was added at a rate maintaining the temperature ≤10° C. The reaction mixture was warmed to room temperature. Upon reaction completion, water (10 mL, 1 vol) was added. CPME (100 mL) and then 1N aqueous NaOH (100 mL) were added. The mixture was stirred for 30 min and the layers were cut. The organic layer was consecutively washed with 1N aqueous NaOH (100 mL), 1N aqueous NH$_4$OH (2×100 mL), and saturated aqueous NH$_4$Cl (50 mL). The organic layer was washed with 14% aqueous NaCl (25 mL) and then concentrated to minimum stir volume at 65° C. under vacuum. CPME (100 mL) was added and the solution was distilled to minimum stir volume. CPME (100 mL) was added and the solution is distilled to minimum stir volume. CPME (100 mL) was added and the solution was heated to 50° C. Charcoal (7.35 g) was added. The mixture was stirred at 50° C. for 12 hours. The charcoal was filtered and the solution was distilled to minimum stir volume and CPME and heptane were added to obtain a final solution of 80 mL (8 vol) of a 35% CPME/heptane mixture. The mixture was heated to 70° C. to obtain a solution, and then cooled to 55° C. then seeded with 50 mg ((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)(isopropyl)carbamate. The mixture was held at 55° C. for 1 h and then cooled to room temperature. Heptane (29 mL) was added and the mixture was cooled to 0-5° C., filtered and washed with 15% CPME/Heptane (2×15 mL) and heptane (2×15 mL). The filter cake was dried at ≤55° C. to give tert-butyl ((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)(isopropyl)carbamate, isolated 14.1 g, 86% yield.

Example 3

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride To a 500 mL reactor was added tert-butyl ((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)(isopropyl)carbamate (49 g) and 2-propanol (196 mL) and the reactor was heated to 50° C. A solution of HCl in 2-propanol (3M, 90 mL) was added to maintain the temperature from 50-70° C. The solution was maintained at 60° C. for 19 hours and the mixture was cooled to 0-5° C. Amberlyst® A-21 resin (60.5 g) was washed with water (50 mL) and purged with N$_2$ for 5 min to remove excess water. The resin was then washed with 2-propanol (50 mL) and purged with N$_2$ for 5 min to remove excess 2-propanol. The reaction mixture was re-circulated through the packed resin bed for at least 2 hours until pH 3.55-7.0 was reached. The resin bed was purged with N$_2$ for 5 min, collecting all the filtrates. The resin was washed with 2-propanol (294 mL), and the resin was purged with N$_2$ for 5 min, combining all the filtrates. To the combined solution was added decolorizing charcoal (20 g) and the mixture was stirred at 15-25° C. for 1-2 hours. The charcoal was then filtered and the solution was distilled under vacuum at 25-35° C. Charged EtOAc (333.0 mL) to obtain a ~87.5:12.5 EtOAc:2-propanol ratio. A seed slurry (1 g) of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride in EtOAc:IPA (~6 mL, 87.5:12.5) was added to the reactor and the mixture was stirred at 20-25° C. for 1 h. The slurry was constant volume solvent-switched to EtOAc at 20-30° C. until a ratio of EtOAc:2-propanol ≥97:3 was reached. The reactor was cooled to 0-10° C. and the slurry filtered. The filter cake was washed with EtOAc (115 mL) and dried under vacuum at 85° C. for 16 hours to afford (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride as an off-white solid: 41.9 g (94% yield).

Alternative Procedure Using Organic Amine Bases

Using N-methylmorpholine:

To a solution of tert-butyl ((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)(isopropyl)carbamate (5 g) in 2-propanol (317 g) was added HCl in 2-propanol. The solution was heated until complete deprotection. The solution was cooled to room temperature and then a solution of N-methylmorpholine (556.3 mg) was added dropwise. The resulting solid NMM.HCl was filtered off and the filtrate was concentrated and solvent-switched to ethyl acetate. The resulting solid (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride was filtered and washed with ethyl acetate and dried under vacuum (99.8% purity by LC).

Using piperazine:

To a solution of tert-butyl ((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)(isopropyl)carbamate (50 g) in 1-propanol (128 g) was added HCl in 1-propanol (45.2 g, 5.5N). The solution was heated until complete deprotection. The solution was cooled to room temperature and then a solution of piperazine (7.3 g) in 1-propanol (36.5 g) was added dropwise. The resulting solid piperazine.HCl was filtered off and the filtrate was carbon treated, concentrated and solvent-switched to ethyl acetate. The resulting solid (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride was filtered and washed with ethyl acetate and dried under vacuum (Yield 22.9 g, 99.8% purity by LC).

Example 4

Salt Formation of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one (S)-2-(4-Chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one was solid dosed into well plates. Various counter ions were stock dosed in MeOH/water mixtures and dosed into the well plates. Upon addition of the counter ion solution salt formation took place. The stock-solvent solutions were evaporated over several days. The well plates were dried under reduced pressure of 100 mBar for 24 h at rt, and then 10 mbar for 24 h at rt. Solid residues obtained after drying were harvested and subjected to XRPD.

Example 5

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one Benzene Sulfonic Acid Salt (S)-2-(4-Chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one free base (113.99 mg) was dissolved in methyl ethyl ketone (1 mL) Benzenesulfonic acid (39.98 mg) was dissolved in methyl ethyl ketone and the acid solution added to the solution of free base. Solid formed. Additional methyl ethyl ketone was added to ensure that the suspension could be mixed. The suspension was stirred overnight and the benzenesulfonic acid salt was isolated by filtration and dried in a vacuum oven for 2 hours at 50° C.

Figure 1A:
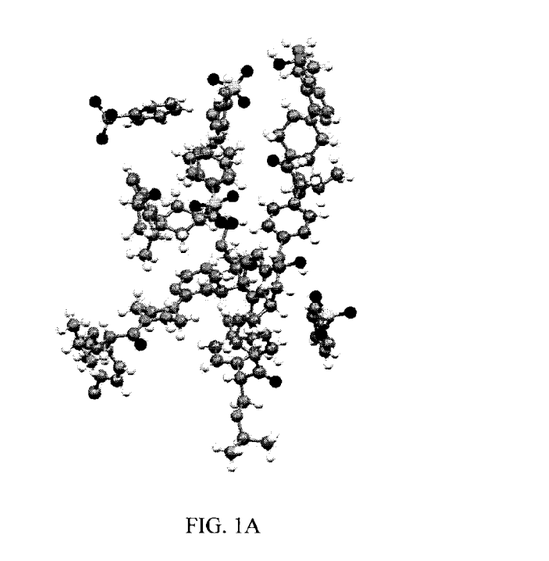
FIG. 1A shows the single crystal structure of the benzenesulfonic acid salt of a compound of formula Ia of Example 5.
Figure 1B:
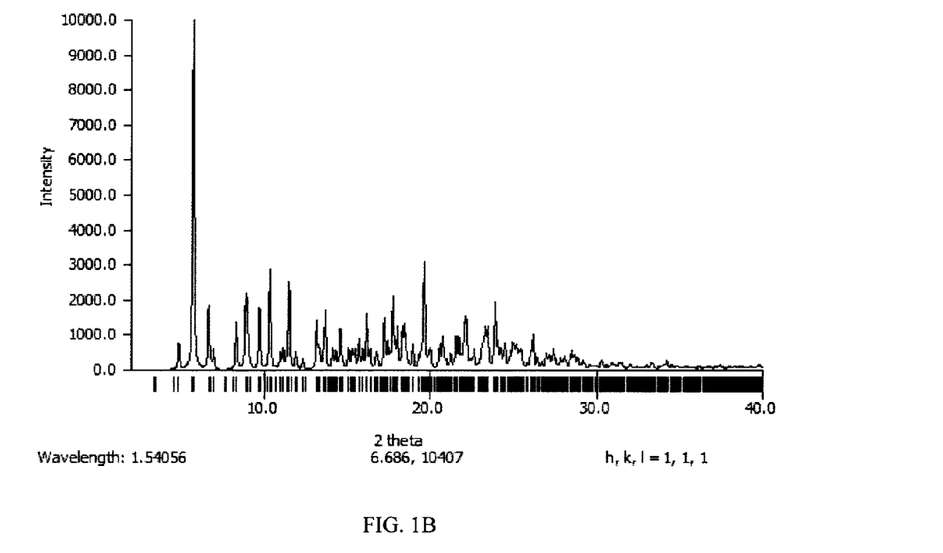
FIG. 1B shows the calculated X-ray diffraction pattern of the single crystal.

The benzenesulfonic acid salt from above, 10.2 mg, was placed into a 20 mL vial, acetonitrile, 0.2 mL, added and the vial placed into a shaking block at 22° C. The slurry was shaken for 8 days to give a mixture of needles and plates. Single crystal structure determination was conducted on one of the plates from the slurry (See FIGS. 1A-1B), and the data is shown in Table 2 below.

TABLE 2

| formula | C30H38Cl1N5O5S1 |
|---|---|
| formula weight | 616.18 |
| space group | P 21 21 21 (No. 19) |
| a, Å | 19.3682(15) |
| b, Å | 25.4177(19) |
| c, Å | 26.121(3) |
| α, deg | 90 |
| β, deg | 90 |
| γ, deg | 90 |
| V, Å$^3$ | 12859.4(19) |
| Z | 16 |
| $d_{calc}$, g cm$^{-3}$ | 1.273 |
| temperature, K | 150 |
| radiation (wavelength, Å) | Cu K$_\alpha$ (1.54184) |
| diffractometer | Nonius_KappaCCD |
| h, k, l range | −22 to 21 −28 to 28 −30 to 30 |
| θ range, deg | 1.69-63.38 |
| programs used | SHELXTL 2008 |
| data collected | 12519 |
| unique data | 12519 |
| R(F$_o$) | 0.098 |
| R$_w$(F$_o^2$) | 0.194 |
| goodness of fit | 1.091 |
| absolute structure determination | Flack parameter (0.01 (3)) |

Figure 2:
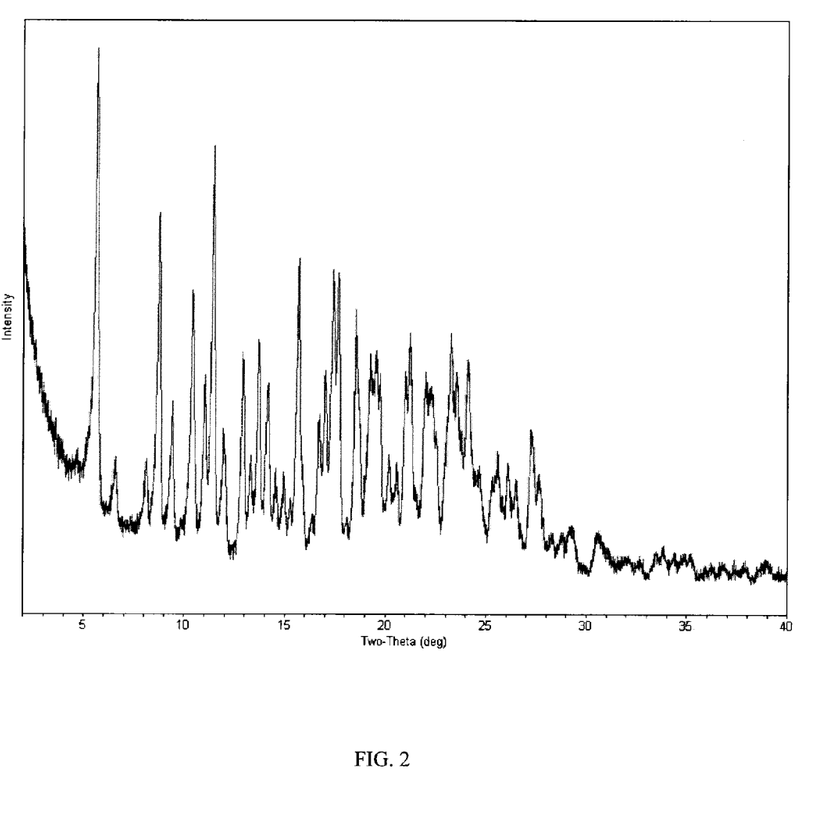
FIG. 2 shows the XRPD of a benzenesulfonic acid salt of a compound of formula Ia of Example 5.

Alternative Procedure:

(S)-2-(4-Chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one free base, 1.47 g, was added to a reactor fitted with overhead stirrer. Methyl ethyl ketone (MEK), 10 mL, was added and the solid dissolved. Benzenesulfonic acid, 454.6 mg, was dissolved in MEK, 10 mL, and the acid solution was added, via syringe, over 10 minutes to the solution of free base. The vial containing the acid solution was rinsed with MEK, 5 mL, and the rinse solution added to the reactor via the syringe. Solid was observed in the reactor after addition of 2-3 mL of the acid containing solution. The suspension was stirred for 3 hours and the solid isolated by vacuum filtration. The solid was dried under reduced pressure (house vacuum, about 50 torr) at 50° C. for 3 hours. The solid was subsampled, 950 mg, and slurried in acetonitrile, 3 mL, overnight at ambient conditions. The slurry was heated to 49° C. for 1 hour and then removed from the heating block and allowed to cool to room temperature on a magnetic stirring plate. The solid was isolated by vacuum filtration. The vial was rinsed with acetonitrile, 2×1 mL, to transfer the solid to the filter. The resulting solid was dried under reduced pressure at 50° C. using house vacuum to give crystalline besylate salt. The product was characterized by XRPD (See FIG. 2).

Example 6

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one p-toluene Sulfonic Acid Salt

Figure 3:
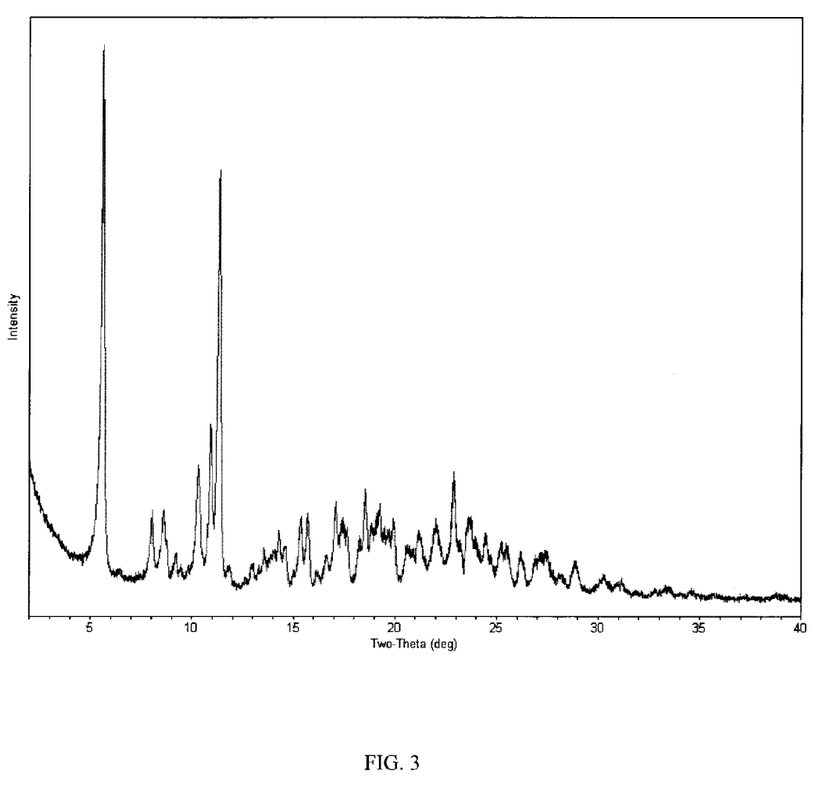
FIG. 3 shows the XRPD of a p-toluenesulfonic acid salt of a compound of formula Ia of Example 6.

(S)-2-(4-Chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one free base, 202.4 mg, was dissolved in acetonitrile, 10 mL. p-Toluenesulfonic acid monohydrate, 83.5 mg, was dissolved in acetonitrile, 10 mg, and the two solutions mixed. The solution was slowly evaporated under a stream of nitrogen. The crystaline tosylate salt was analyzed after evaporating over 3 weeks (See FIG. 3).

We claim:

1. A process comprising contacting a compound of formula II or a salt thereof:

wherein:
$R^1$ is hydrogen or an amino protecting group; with a ketoreductase enzyme or an alcohol dehydrogenase enzyme to form a compound of formula III:

or a salt thereof.

2. The process of claim 1, wherein said ketoreductase or alcohol dehydrogenase enzyme is selected from KRED-101, KRED-112, KRED-113, KRED-114, KRED-115, KRED-121, KRED-123, KRED-124, KRED-130, KRED-132, KRED-133, KRED-135, KRED-142, KRED-145, KRED-153, Codexis-134, Codexis-150, Codexis-168, Codexis-112, Codexis-102, Codexis-151, Codexis-123, Codexis-103, Codexis-119, Codexis-128, Codexis-136, Codexis-174, Codexis-105, Codexis-129, Codexis-137, Codexis-161, Codexis-176, Codexis-154, Codexis-106, Codexis-131, Codexis-155, Codexis-148, Codexis-165, Codexis-129, Codexis-108, Codexis-116, Codexis-125, Codexis-149, Codexis-111, DAICEL-E073, DAICEL-E087, BCC 111, C-LEcta-ADH-44s, DAICEL-E005, DAICEL-E077, C-LEcta-ADH-24 s, BCC 103, C-LEcta-ADH-14s, C-LEcta-ADH-16s, DAICEL-E007, DAICEL-E008, DAICEL-E080, DAICEL-E082, DAICEL-E052, BCC 101, C-LEcta-ADH-48s, BCC 109, EVO-1.1.211, DAICEL-E072, ADH-1, ADH-2, ADH-3, ADH-A, ADH-B, ADH-III and C-LEcta-ADH-50 s.

3. The process of claim 1, wherein said ketoreductase is KRED-101.

4. The process of claim 1, wherein said contacting step further comprises contacting a compound of formula II or a salt thereof with cofactor.

5. The process of claim 4, wherein said cofactor comprises one of NADP, NADH, NADPH or GDH.

6. The process of claim 4, wherein said cofactor comprises NADP and GDH.

7. The process of claim 1, further comprising reacting a compound of formula III or salt thereof wherein $R^1$ is an amino protecting group with acid to form a compound of formula Ma or salt thereof:

8. The process of claim 7, further comprising reacting a compound of formula Ma or salt thereof with a compound of formula IV or salt thereof under conditions that form a compound of formula I or salt thereof, wherein R² in formulae IV and I is independently hydrogen or amino protecting group, and said conditions comprise propanephosphonic anhydride.

9. The process of claim 8, further comprising reacting a compound of formula I or salt thereof, wherein R² is amino protecting group, with acid to form a dihydrochloride salt of a compound of formula I, wherein R² is hydrogen.

10. The process of claim 9, further comprising contacting the dihydrochloride salt of compound of formula I with base to form a monohydrochloride salt of a compound of formula I, wherein R² is hydrogen.

11. The process of claim 10, wherein said base is a polymeric resin comprising a functionalized styrene divinylbenzene copolymer.

12. The process of claim 1, further comprising reacting a compound of formula III or salt thereof, wherein R₁ is hydrogen, with a compound of formula IV or salt thereof under conditions that form a compound of formula I or salt thereof, wherein R² in formula IV and I is independently hydrogen or amino protecting group, and said conditions comprise propanephosphonic anhydride.

13. The process of claim 12, further comprising reacting a compound of formula I or salt thereof, wherein R² is amino protecting group, with acid to form a dihydrochloride salt of a compound of formula I, wherein R² is hydrogen.

14. The process of claim 13, further comprising contacting the dihydrochloride salt of compound of formula I with base to form a monohydrochloride salt of a compound of formula I, wherein R² is hydrogen.

15. The process of claim 14, wherein said base is a polymeric resin comprising a functionalized styrene divinylbenzene.

16. The process of claim 1 comprising contacting a compound of formula II or a salt thereof with a ketoreductase enzyme.

* * * * *